United States Patent [19]

Meland et al.

[11] 4,227,516

[45] Oct. 14, 1980

[54] APPARATUS FOR ELECTROPHYSIOLOGICAL STIMULATION

[76] Inventors: Bruce C. Meland, 4525 Matilija Ave., Sherman Oaks, Calif. 91423; Bernard C. Gindes, deceased, late of Los Angeles, Calif.; by Hanna Gindes, executrix, 616 Hanley Ave., Los Angeles, Calif. 91423

[21] Appl. No.: 969,104

[22] Filed: Dec. 13, 1978

[51] Int. Cl.³ ............................................. A61M 21/00
[52] U.S. Cl. ..................................................... 128/1 C
[58] Field of Search ................................ 128/1 C, 1 R

[56] References Cited

U.S. PATENT DOCUMENTS

| | | | |
|---|---|---|---|
| 2,986,140 | 5/1961 | Gardner et al. | 128/1 R |
| 3,255,753 | 6/1966 | Wing | 128/1 C |
| 3,718,132 | 2/1973 | Holt et al. | 128/1 C |
| 3,753,433 | 8/1973 | Bakerich et al. | 128/1 C |
| 3,762,396 | 10/1973 | Ballentine et al. | 128/1 C |
| 3,884,218 | 5/1975 | Monroe | 128/1 C |
| 3,908,634 | 9/1975 | Monaghan | 128/1 C |
| 4,047,377 | 9/1977 | Banks, Jr. | 128/1 C |

*Primary Examiner*—William E. Kamm
*Attorney, Agent, or Firm*—Keith D. Beecher; Jessup & Beecher

[57] ABSTRACT

Apparatus for the electrophysiological stimulation of a patient is provided for creating an analgesic condition in the patient to induce sleep, treat psychosomatic disorders, and to aid in the induction of electrohypnosis and altered states of consciousness. The foregoing is achieved by repetitive stimuli in the patient for whom external influences, namely those of sight and sound, are intentionally excluded. The apparatus produces electrical stimulation of the patient in the form of a modulated wave which produces impulses in the delta, theta, alpha and beta regions of the brain's electrical activity, the electrical stimulation being accompanied by two sources of audio stimulation, one of which is a sinusoidal tone modulated by and synchronized with the electrical stimulation, and the other is derived from sound recordings.

15 Claims, 3 Drawing Figures

APPARATUS FOR ELECTROPHYSIOLOGICAL STIMULATION

BACKGROUND

Methods and apparatus are known for inducing sleep, treating psychosomatic disorders, and for aiding in the induction of hypnosis in a patient, the foregoing being achieved by passing a stimulation of electrical current pulses through the brain of the patient by electrodes attached, for example, to the back of the head and to the forehead. Such apparatus is described, for example, in U.S. Pat. No. 3,762,396. In the apparatus described in the patent, the electric current impulses of the stimulus have a frequency of 8-10 Hz. The apparatus described in the patent also passes a second stimulus of electric pulses to the brain of the patient having a frequency which is four times the frequency of the pulses of the first stimulus, the latter stimulus being introduced through the optic nerves of the patient by the electrodes attached to the temple and forehead. A third auditory stimulus is provided in the system described in the patent by way of sound attenuating chambers. The auditory stimulus is used acoustically to isolate the patient from a noise environment. The three stimuli are preferably synchronized with one another.

U.S. Pat. No. 3,908,634 describes a method and apparatus for inducing a vocalized analgesic condition in the patient by simulating the presence of a hypnotherapist. This is achieved by reproducing a recording of the speech that the hypnotherapist would normally make to the patient.

The apparatus of the present invention falls in the same general class as the apparatus described in the above-mentioned patents; and an objective of the apparatus of the invention, likewise, is to produce different states of consciousness in a patient by repetitive stimuli, with the patient being insulated from external influence. In the practice of the invention, the patient to all intents and purposes is placed in a closed chamber in which the apparatus is set to an operational mode which creates a sensory input; and impulses in the delta, theta, alpha and beta ranges are introduced to the optic cortex, each producing its specific state of consciousness in the patient.

The various ranges referred to above relate to the different rhythms in the brain's electrical activity. For example, the alpha rhythms have a pulse frequency in the 8-13 Hz range; the beta rhythms have a pulse frequency in the 13-30 Hz range; the theta rhythms have a pulse frequency in the 4-7 Hz range; and the delta rhythms are slow waves with pulse frequencies in the 0.5-3 Hz range. The alpha rhythms are customarily found in the normal human adult when he is relaxed and has his eyes closed; the beta rhythms are normally encountered when a person is aroused and anxious; the theta rhythms are often found in adolescents with behavior disorders; and the delta rhythms appear in the normal person when he is asleep.

Each impulse introduced to the patient by the apparatus of the invention is super-imposed on the brainwave activity, finally dominating it and thereby altering the patient's state of awareness. The result is light or deep sleep, somnolence, hypnosis, heightened awareness, or even agitation, depending upon the frequency of the pulses introduced to the patient.

The electrical stimulation is in the form of a modulated square wave accompanied by two sources of audio stimulation, one of which is a sinusoidal tone, modulated by and synchronized with the optical electrical stimulation. The other audio sound helps to overwhelm the circuits, minimizing internal and external inputs. The subject is restricted to the selective sensory impulses he is receiving, and he shuts out most of his internal and external environment, the result being that the impulses received alter the patterns of brain activity essentially bringing the brain into synchronism with the instrument.

Specifically, the present invention provides an improved instrument constructed for electrophysiological stimulation of a human being. The instrument is capable of inducing into the patient the effects produced by brainwave activity in the delta, theta, alpha and beta ranges. The apparatus uses a modulated square wave which creates the electrophysiological stimulation, and which is accompanied by two sources of audio stimulation, one being synchronized with the electrophysiological stimulation. The electrical stimulation is applied to the patient by means of electrodes attached to the forehead.

The audio stimulation is introduced to the patient by means of headphones. One of the audio stimuli is a sinusoidal tone modulated by and in synchronism with the electrophysiological stimulation. The other audio stimulus is derived from a cassette tape player, which plays pre-recorded tapes of special sound effects or hypnotic suggestions recorded for a specific patient.

The result of the foregoing three stimulating forces acting together enables the instrument to alter the mood or mental state of the patient so as to produce a variety of altered mental states. The instrument of the invention can be used, for example, for inducing sleep, inducing an hypnotic state, producing tranquility and relaxation, producing heightened awareness, increasing the ability of a person to concentrate, and for inducing other mental states. The instrument can also be used for treating psychosomatic disorders.

The instrument to be described is battery operated from a self-contained rechargeable 12-volt battery. Battery operation is used for electrical safety, since it completely eliminates the possibility of a patient being electrocuted, as could occur with alternating current line operated equipment.

DETAILED DESCRIPTION OF THE ILLUSTRATED EMBODIMENT

Figure 1:
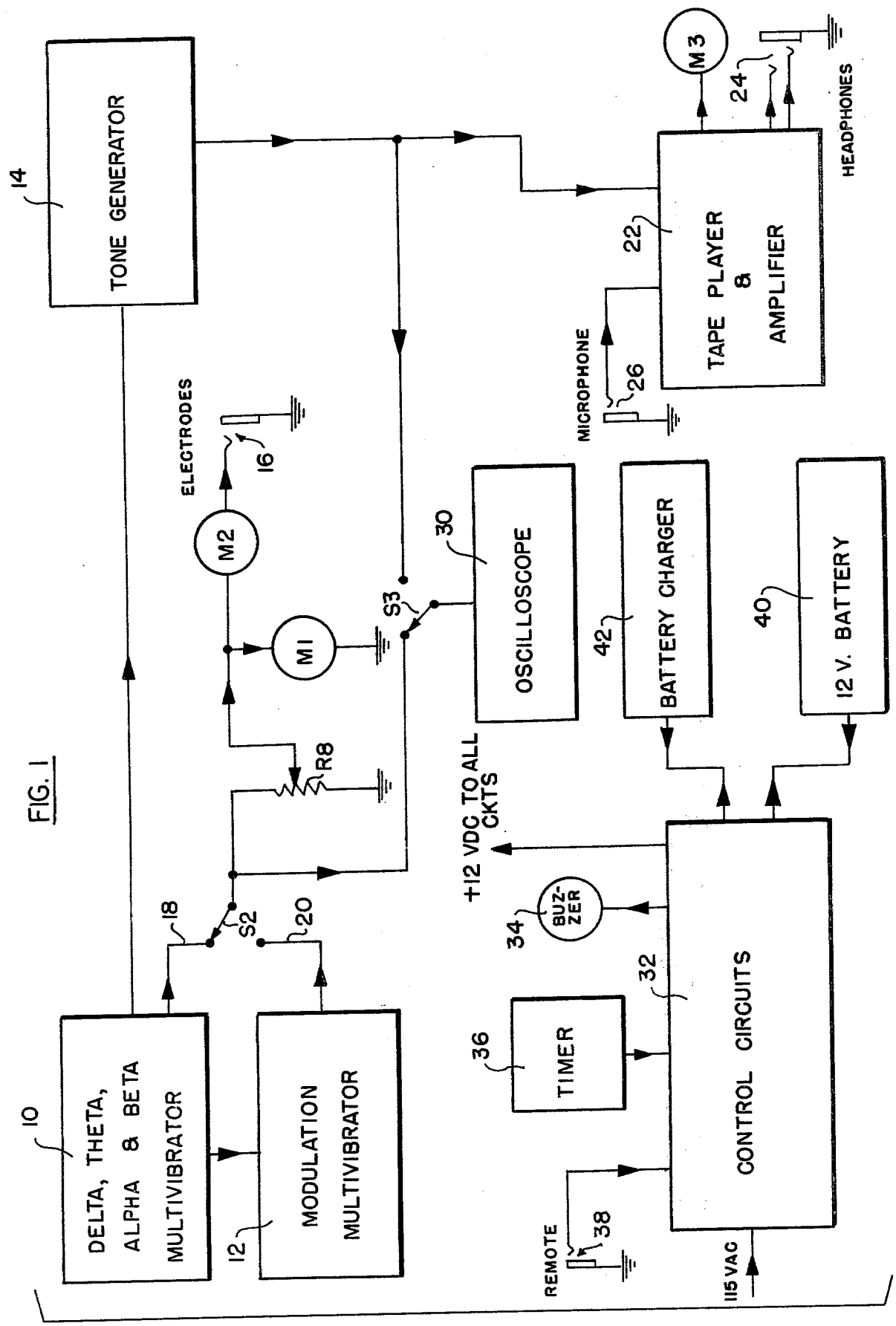
FIG. 1 is a block diagram of an instrument representing one embodiment of the invention.

The system of the invention includes a block designated 10 which is the nucleus of the system. This block is an astable multivibrator which generates square waves of variable frequency and shape. The multivibrator of block 10 performs three functions: (1) it controls or synchronizes the output of a modulation multivibrator represented by block 12; (2) it controls or synchronizes the output of a tone generator represented by block 14; and (3) it produces square wave output pulses which can be used as the stimulating voltage applied to the patient by way of electrodes connected to a jack 16.

The square wave output from the multivibrator of block 10 appears on a lead 18 which is connected to one of the fixed contacts of a switch S2. The modulated pulse output of the modulation multivibrator of block 12 appears on a lead 20 which is connected to the other fixed contact of switch S2. The armature of switch S2 is connected to a grounded potentiometer R8 and to a fixed contact of a switch S3. The armature of potentiometer R8 is connected to a grounded voltmeter M1, and through an ammeter M2 to jack 16 which receives an appropriate plug to connect the circuit to an electrode on the forehead of the patient. The output of tone generator 14 is connected to a second fixed contact of switch S3, and the armature of the switch is connected to an oscilloscope represented by the block 30.

The synchronized sinusoidal tone derived from the tone generator of block 14 is applied to a tape player and amplifier 22 so as to synchronize one of the outputs from the amplifier with the square wave pulses from the multivibrator 10. A further meter designated M3 is connected to the tape player and amplifier 22. The synchronized sinusoidal output from the tape player and amplifier 22 is applied to one of the contacts of a headphone jack 24. The recorded message of hypnotic suggestions for the specific patient is also recorded in the tape player, and signals representing these messages are introduced to a second contact on jack 24. New messages may be recorded by a microphone having a plug which is plugged into a microphone jack 26.

Direct current power for the instrument is provided by control circuits represented by the block 32, the control circuits also controlling a buzzer 34, and being controlled by a timer 36. A remote control may also be connected to the control circuits by way of a jack 38. The control circuits are activated by a 12-volt battery 40 which is maintained in a charged condition by a battery charger 42, the battery charger being energized by the usual 115-volt alternating current voltage derived from the usual alternating current mains.

Figure 2A:
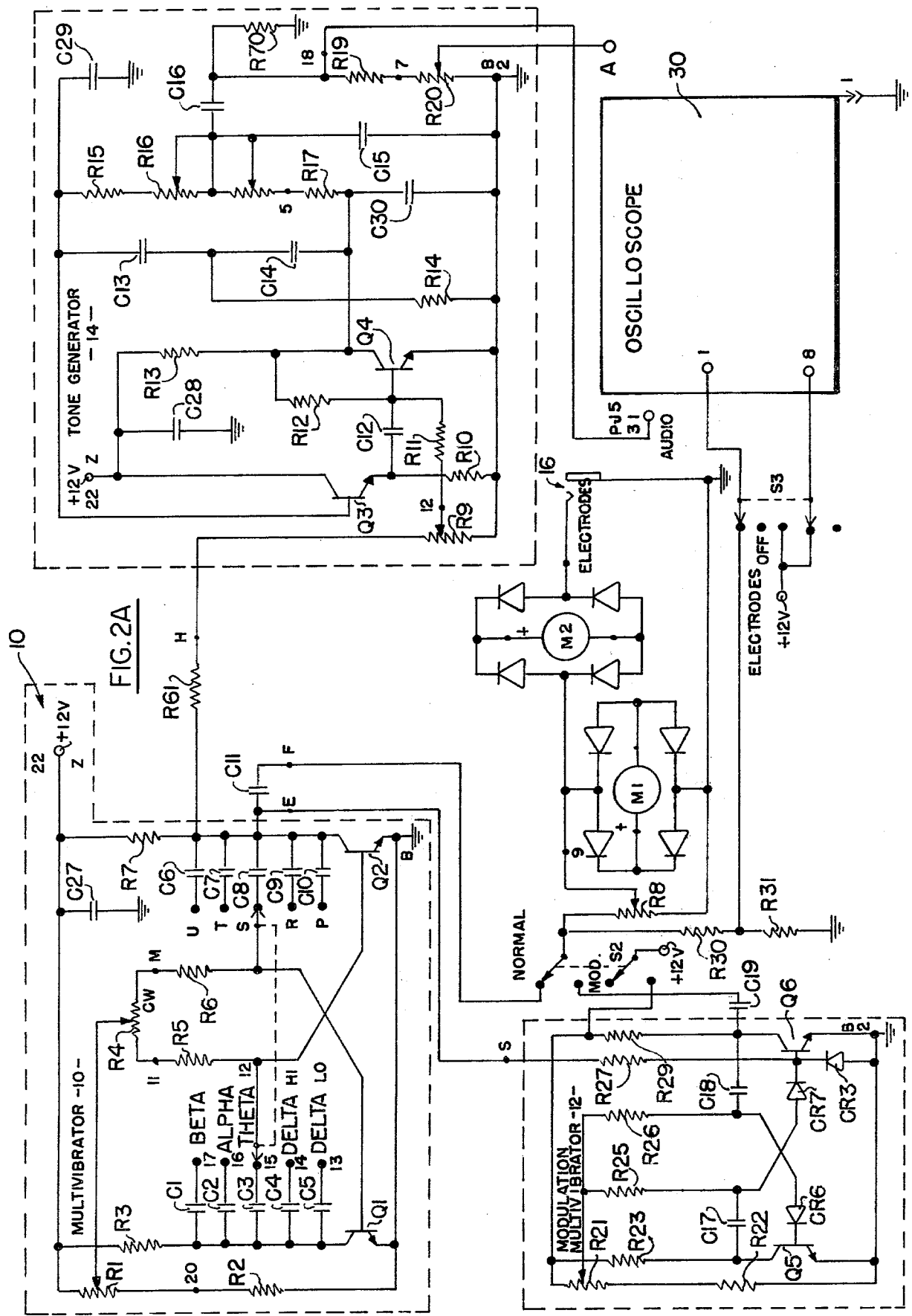
FIGS. 2 and 2A represent a circuit diagram of the instrument of FIG. 1.

As shown in FIG. 2A, the multivibrator 10 includes a pair of NPN transistors Q1 and Q2 which are interconnected through a 10 kilo-ohm potentiometer R1, a 3.9 kilo-ohm resistor R2, a 2.2 kilo-ohm resistor R3, a 50 kilo-ohm potentiometer R4, a 4.7 kilo-ohm resistor R5, a 4.7 kilo-ohm resistor R6, and a 470 ohm resistor R7. The multivibrator 10 also includes a two-pole operator control switch S1 which makes selective contact with a first group of capacitors C1, C2, C3, C4 and C5 having respective capacities of 1, 1.9, 4.5, 10.7 and 39 microfarads, and a second group of capacitors C6, C7, C8, C9 and C10 having respective capacitires of 1, 1.9, 4.5, 10.7 and 39 microfarads. Also included in the circuit of multivibrator 10 is a 1000 microfarad capacitor C27 and a 250 microfarad capacitor C11.

The modulation multivibrator 12 includes a pair of NPN transistors Q5 and Q6 which are interconnected through a pair of diodes CR6 and CR7, and through a 10 kilo-ohm resistor R21, a 4.7 kilo-ohm resistor R22, a 2.2 kilo-ohm resistor R23, a 47 kilo-ohm resistor R25, a 47 kilo-ohm resistor R26, a 50 kilo-ohm resistor R27, and a 470 ohm resistor R29. Also included in the multivibrator circuit are a 0.33 microfarad capacitor C17, a 0.33 microfarad capacitor C18, and a 50 microfarad capacitor C19.

The capacitor C11 of the multivibrator 10, and the capacitor C19 of the modulation multivibrator 12 are connected to a switch S2 which, in turn, is connected to the jack 16 through the meters M1 and M2.

The switch S3 associated with oscilloscope 30 is connected to the junction of a 240 kilo-ohm resistor R30, and a 68 kilo-ohm resistor R31, the resistors being connected between one of the contacts of switch S2 and ground, as shown.

The multivibrator 10 is connected through a 47 kilo-ohm resistor R61 to a 7.5 kilo-ohm potentiometer R9, the latter potentiometer being included in the circuit of tone generator 14. The tone generator includes a pair of NPN transistors Q3 and Q4 which are interconnected by a 4.7 kilo-ohm resistor R10, a 15 kilo-ohm resistor R11, a 150 kilo-ohm resistor R12, and a 3.3 kilo-ohm resistor R13. Also included in the circuit are a 500 microfarad capacitor C28 and a 0.1 microfarad capacitor C12.

The transistor Q4 is connected to a resistance-capacitance network which includes a 1 kilo-ohm resistor R14, and a pair of 0.15 microfarad capacitors C13 and C14. The transistor Q4 is also connected to a 4.7 kilo-ohm resistor R17, a pair of 10 kilo-ohm potentiometers designated R16, and a 4.7 kilo-ohm resistor R15. Also included in the latter network are a 0.01 microfarad capacitor C30 and a 0.1 microfarad capacitor C15. The circuit also includes a 25 kilo-ohm potentiometer R20, a 100 kilo-ohm resistor R19, and a 15 kilo-ohm resistor R70. Included in the latter circuit are a 0.01 microfarad capacitor C29 and a 0.22 microfarad capacitor C16.

Figure 2B:
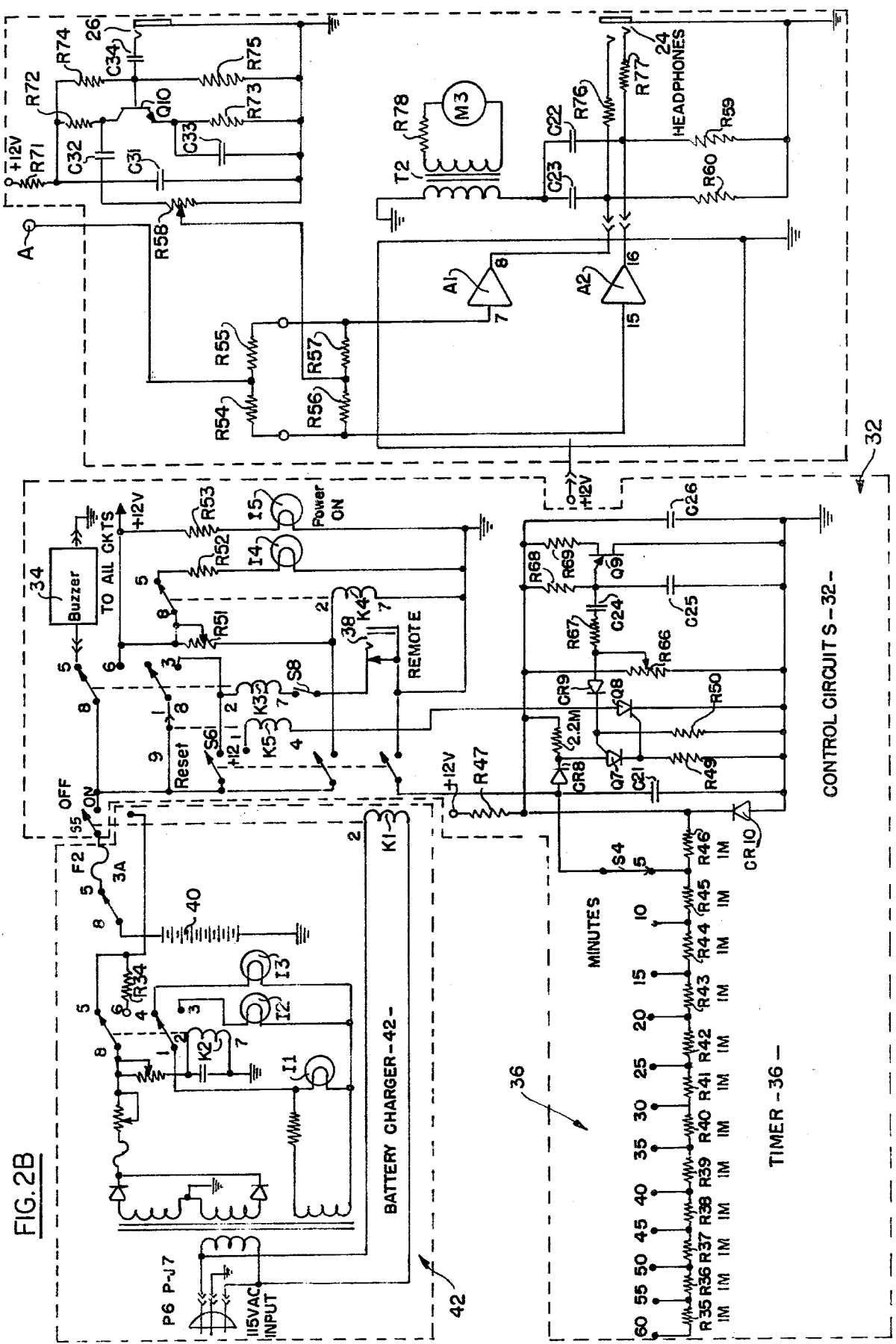

The battery charger circuit 42 is of usual construction, and has a circuit such as shown in FIG. 2B. This circuit is used to maintain a full charge on battery 40. The battery is connected to the control circuits 32 through a switch S5, and through a switch S6. The control circuits include relays K3 and K5, one pair of contacts of relay K3 being connected to the buzzer 34. The control circuits also include a 1 kilo-ohm potentiometer R51, and a pair of 68 ohm resistors R52 and R53. A further relay K4 is also included in the control circuit, as are a pair of indicating lights I4 and I5. Relay K3 is connected to jack 28 which receives a remote control for the system.

The control circuits 32 also include a unijunction transistor Q7, and a silicon controlled rectifier Q8. The unijunction transistor may be of the type designated 2N6027, and the silicon controlled rectifier may be of the type designated C103. Associated with the unijunction transistor and the silicon controlled rectifier are a 100 ohm resistor R49, a 3.3 megohm resistor R50, a 2.2 megohm resistor R65, a 1 megohm potentiometer R66, a 1 megohm resistor R67, a 1 megohm resistor R68, and a 1 kilo-ohm resistor R69. Also included in the control circuits are a pair of diodes CR8 and CR9, a capacitors C21, a 0.001 microfarad capacitor C24, a 1 microfarad capacitor C25, and a 0.01 microfarad capacitor C26. A blank transistor Q9 is also included in the circuit, and may be of the type designated TIS43.

The control circuits are connected to the timer 36 through diode CR8, and through a further diode CR10. The latter diode is connected to the positive terminal of a 12-volt source through a 680 ohm resistor R47. The timer comprises a series of 1 megohm resistors R35-R46, and a switch S4 which is controllable to connect selectively with the junctions between the resistors.

The tape player and amplifiers 22 include a pair of amplifiers A1 and A2. Inputs from the microphone plugged into jack 26 are amplified in an amplifier including an NPN transistor Q10. The amplifier includes a 10 kilo-ohm resistor R58, a 4.7 kilo-ohm resistor R72, a 470 ohm resistor R43, and 82 kilo-ohm resistor R74 and a 10 kilo-ohm resistor R75. The amplifier also includes a 10 microfarad capacitor C32, a 100 microfarad capacitor C33, and a 1000 microfarad capacitor C31. A voice volume 10 kilo-ohm potentiometer R58 is connected across the output of the amplifier, and is connected to the junction of a pair of 22 kilo-ohm resistors R56 and R57 which, in turn, are connected to the inputs of the amplifiers A1 and A2. The tone volume control potentiometer R20 of the tone generator 14 is connected to a pair of 22 kilo-ohm resistors R54 and R55 which, likewise, are connected to the inputs of the amplifiers. The amplifiers are connected to the headphone jack 24 through a pair of 220 ohm resistors R76 and R77, and to a pair of 4 ohm resistors R59 and R60. The amplifiers are also coupled to audio level meter M3 through a pair of 50 microfarad capacitors C22 and C23, through a transformer T2, and through a 33 kilo-ohm resistor R78.

The frequency range of multivibrator 10 is controlled by the operator control switch S1, to set the frequency in the "delta low", "delta hi", "theta", "alpha" and "beta". The frequency is more precisely adjusted in each of the aforesaid ranges by the operator control potentiometer R1. The shape, or symmetry of the square wave is adjusted by the operator control potentiometer R4.

When the pulses from potentiometer 10 are used as the stimulating voltage, the operator control switch S2 is set to the upper position designated "normal". The amplitude of the pulses generated by the multivibrator are controlled by the operator control potentiometer R8. The voltage and current output are monitored by the control panel meters M1 and M2 respectively, with M1 monitoring the electrode voltage, and M2 monitoring the electrode current. The square wave output at jack 16 is an alternating current, whose direct current component is blocked by capacitor C11.

If desired, oscilloscope 30 may be incorporated into the circuit so that the actual square wave shape may be observed, and so that its frequency may be measured.

The electrodes which are attached to the patient's forehead by means, for example, of a rubber strap, receive their voltage by means of suitable wires connected to the jack 16. The modulation multivibrator 12, like modulator multivibrator 10 is an astable multivibrator. Multivibrator 12 is similar to multivibrator 10 except that it has a limited frequency range, and in that it has a fixed pulse shape which is a symmetrical square wave. The frequency range of multivibrator 12 is from 23 to 50 Hz, and the frequency is controlled by the operator control potentiometer R21. The output voltage of modulation multivibrator 12 is turned on and off by square wave pulses received from multivibrator 10. These controlling pulses are applied to the base of transistor Q6 causing it to become conductive and thereby stopping the multivibrator action during each positive pulse. The negative pulses are blocked from the base of transistor Q6 by diode CR3.

The net result is the effect of a modulated output from multivibrator 12 which consists of bursts of higher frequency square waves, the burst rate being controlled by multivibrator 10. The output of multivibrator 12 can be used as the stimulating voltage, when the output is selected by the control switch S2, when the control switch is switched to its lower position. The amplitude of the output from the modulation multivibrator 12 is controlled by the same potentiometer R8 which also controls the output from multivibrator 10. The same meters M1 and M2, and oscilloscope 30 monitor the output from the modulation multivibrator 12, and the output is available at the same jack 16, for application to the electrodes on the head of the patient.

The frequency of 23-50 Hz of each burst produced by the modulated multivibrator 12 produces the maximum amount of flicker images in the optic system of the patient. The output of multivibrator 12 is also an alternating current signal, with the direct current component being blocked by the capacitor C19.

The tone generator 14 is a sinusoidal tone generator, the output of which can be varied in frequency by the operator control potentiometer R16 over a range of 150-600 Hz. The tone is modulated by the square wave output of multivibrator 10. The controlling pulses from multivibrator 10 are applied to the base of transistor Q4. Each positive pulse from the multivibrator renders the transistor Q4 conductive, either partially or completely to saturation, thereby slightly changing the frequency or completely stopping the oscillation of the tone generator.

The degree of modulation is adjustable by the operator control potentiometer R9. This potentiometer can be adjusted for complete turn-off producing tone bursts or partial turn-off producing an undulating tone. The potentiometer can also be adjusted for zero modulation producing a continuous steady tone. The volume of the tone can be adjusted by the operator control potentiometer R20. Since the tone generator is controlled by the output of multivibrator 10, its output is in exact synchronism with the stimulation produced by the electrodes plugged into jack 16. The three controls, namely tone frequency, tone modulation and tone volume can therefore be adjusted by the operator for the most desirable and optimum audio stimulation.

The tape player of block 22 is a stereo cassette tape player, and the block also includes the stereo audio amplifiers A1 and A2. The details of the tape player and amplifiers are not described herein, as they are conventional. The tape player plays standard cassettes of pre-recorded sound effects or vocal suggestions recorded for a specific patient. The amplifier transistor Q10 is used to amplify the microphone input from jack 26, so as to enable the operator to communicate directly with the patient. The output from the amplifier is transmitted to the patient by means of the stereo headphones which are plugged with jack 24.

The output of the tape player is amplified by amplifiers A1 and A2, prior to being introduced to jack 24. The amplifiers A1 and A2 also serve to amplify the tone signals received from the tone generator 24. The output level of all the audio sources is monitored by the control panel meter M3.

All of the control and logic circuitry is contained in block 32, and this circuitry provides automatic controls for charging the battery 40. The control circuit also provides a safety interlock which makes the overall system inoperative whenever the power is connected to the alternating current power line, rather than to the battery. The control circuit receives inputs from a hand held switch S8, and from the timer 36. The timer can be set by adjustment of switch S4. The patient holds switch S8 during therapy, and if the stimulation should become uncomfortable for any reason, the patient can operate the switch which momentarily removes power from relay K3 thereby causing the relay to unlatch removing power from all circuits and energizing buzzer 34 to call the operator. When the pre-set time interval of timer 36 has elapsed, the relay K3 unlatches with the same results.

The indicator lights I1 and I2 are mounted on the control panel to indicate the following conditions to the operator: (a) the indicator light I1 is energized whenever the alternating current power cord is connected to the power line. (b) The indicator lamp I5 is energized when the operator control switch S5 is switched to the on position, and the operator control switch S6 is momentarily depressed. This causes the relay K3 to pull in and "latch" itself in the energized position turning power on to all circuits. (c) The indicator lamp I4 is energized when the batteries are discharged to a point that they are usable only for about two more hours of operation. (d) The indicator lamp I3 is energized when the alternating current power cord is connected and the batteries are being charged. (e) The indicator lamp I2 is energized when the batteries are fully charged.

The battery 19 may be a rechargeable battery pack consisting of two or three parallel connected batteries, each of which has a capacity, for example, of 4.5 ampere hours.

The battery charger 42 may be a conventional circuit.

When the battery voltage drops, for example, to 11.5 volts, indicator lamp I4 in the control circuit 32 is energized, as relay K4 drops out. Relay K4 may be adjusted to drop out at 11.5 volts by potentiometer R51. The battery charge circuit 42 includes an indicator lamp I1 which is energized when the alternating current cord is connected to the line. The circuit also includes an indicator lamp I2 which turns on when battery 40 is fully charged, and an indicator lamp I3 which is energized while the battery is being charged. The charger circuit includes a relay K1 which is energized when the charger is operating, and which disconnects the battery 40 from the system of the invention, and connects it across the battery. The circuit also includes a relay K2 which is energized when the battery 40 is fully discharged, and which, when energized, introduces a 47 ohm resistor R34 into the charging circuit which reduces the charging current sufficiently so that battery 40 is merely maintained in a fully charged condition.

The timer 36 is adjustable, for example, in five minute increments from five minutes to sixty minutes by operation of the control switch S4. The time interval selected begins when the operator control switch S6 marked reset is momentarily depressed. At the end of the time interval selected, relay K5 pulls in, removing power from relay K3 and causing it to unlatch, effectively turning off all power and turning on buzzer 34 to call the attention of the operator.

The timer circuit 36 utilizes the resistance-capacitance time charging principle. Capacitor C21 is the timing capacitor, and resistors R35-R46 are the timing resistors. When capacitor C21 charges up to a sufficiently high voltage, unijunction transistor Q7 is rendered conductive, and applies a trigger pulse to the gate of silicon controlled rectifier Q8, rendering the silicon controlled rectifier conductive. When silicon controlled rectifier Q8 is rendered conductive, it energizes relay K5, producing the results described above. The transistor Q7 is a programmable unijunction transistor, whose intrinsic stand-off ratio is adjusted by potentiometer R66, and which provides a means for calibrating the timer.

A field effect transistor Q9 is connected as an oscillator which provides sampling pulses at the rate, for example, of one per second, and each having a duration of 10 microseconds. These pulses are applied to the gate of transistor Q7, to cause Q7 to become conductive for the duration of one such pulse, when the potential across capacitor C21 exceeds a predetermined threshold. This sampling circuit materially reduces the trigger current required to render the transistor Q7 conductive. Between pulses, the transistor Q7 is isolated from the capacitor C21 by diode CR8, which is a low leakage diode, thereby eliminating any loss of charging current due to leakage through the transistor Q7.

The invention provides, therefore, an improved instrument for electrophysiological stimulation of a patient, and which is constructed to produce stimulation and to stimulate the effect produced by brain wave activity in the delta, theta, alpha and beta range.

It will be appreciated that although a particular embodiment of the invention has been shown and described, modifications may be made. It is intended in the claims to cover the modifications which come within the spirit and scope of the invention.

What is claimed is:

1. A system for producing electrophysiological stimulations in a patient so as to stimulate the effects of brain wave activity in at least one of the delta, theta, alpha and beta frequency ranges, said system including: first means for generating a first wave in a predetermined frequency range extending above the delta, theta, alpha and beta frequency ranges; second means for generating a second wave in at least one of said delta, theta, alpha and beta frequency ranges and connected to said first means to cause the first wave to be modulated by the second wave to cause the first means to produce bursts of the first wave occurring at the frequency of the second wave; and means connected to the first means for introducing the bursts of the first wave from the first means to electrode means mounted on the forehead of the patient for the electrophysiological stimulation of the patient.

2. The system defined in claim 1, in which said first and second means each comprises an astable multivibrator, and in which said first and second waves are square waves.

3. The system defined in claim 2, in which said first means generates the first square wave in a frequency range extending substantially from 23 to 50 Hz.

4. The system defined in claim 2, in which said second means includes manually adjustable means for setting the frequency of the second wave selectively to the delta, theta, alpha and beta frequency ranges.

5. The system defined in claim 2, in which said second means includes manually adjustable means for controlling the shape and symmetry of the second square wave.

6. The system defined in claim 1, and which includes potentiometer means connected to the second means for controlling the amplitude of the modulated wave introduced to the electrode.

7. The system defined in claim 1, and which includes third means for generating a sinusoidal tone signal in a range extending substantially from 150-600 Hz, and including means connected to said second means for modulating the tone signal in synchronism with the second wave generated by the second means; and further means connected to said third means for applying the modulated tone signal to headphones worn by the patient.

8. The system defined in claim 7, in which said third means includes manually controllable means for adjusting the degree of modulation of said tone signal by said second wave.

9. The system defined in claim 7, in which said third means includes manually controllable means for adjusting the frequency of said tone signal.

10. The system defined in claim 7, in which said third means includes manually controllable means for adjusting the volume of the modulated tone signal.

11. The system defined in claim 7, and which includes fourth means connected to said further means for introducing prerecorded sounds to the headphones.

12. The system defined in claim 1, and which includes battery means for energizing the system; and which further includes charging circuitry for the battery means, and control circuitry for de-energizing the system whenever the charging circuitry is active.

13. The system defined in claim 1, and which includes switching means to be held in the hand of the patient to de-energize the system should the stimulation produced by the system become uncomfortable.

14. The system defined in claim 13, and which includes buzzer means connected to the system to be energized when the system is de-energized by said switching means.

15. The system defined in claim 1, and which includes pre-settable timer circuitry for determining the time during which the system is to be activated.

* * * * *